United States Patent
Kopta

(10) Patent No.: US 9,922,730 B2
(45) Date of Patent: Mar. 20, 2018

(54) ASSESSING THE EFFECTIVENESS OF PSYCHIATRIC MEDICATION IN PHYSICIANS' PRACTICES

(76) Inventor: Stephen Mark Kopta, Newburgh, IN (US)

( * ) Notice: Subject to any disclaimer, the term of this patent is extended or adjusted under 35 U.S.C. 154(b) by 1362 days.

(21) Appl. No.: 12/932,093

(22) Filed: Feb. 17, 2011

(65) Prior Publication Data

US 2011/0213557 A1 Sep. 1, 2011

Related U.S. Application Data

(60) Provisional application No. 61/338,290, filed on Feb. 17, 2010.

(51) Int. Cl.
*G06F 19/00* (2018.01)
*G06Q 50/24* (2012.01)

(52) U.S. Cl.
CPC ......... *G16H 10/20* (2018.01); *G06F 19/3456* (2013.01); *G16H 15/00* (2018.01); *G16H 50/30* (2018.01); *G16H 50/70* (2018.01)

(58) Field of Classification Search
None
See application file for complete search history.

(56) References Cited

U.S. PATENT DOCUMENTS

2005/0119534 A1* 6/2005 Trost et al. ............. 600/300
2006/0229505 A1* 10/2006 Mundt et al. .......... 600/300
2008/0243550 A1* 10/2008 Yao ......................... 705/3

OTHER PUBLICATIONS

Worthen, "Outcome oriented supervision: Advantages of adding systematic client tracking to supportive consultations," Counselling and Psychotherapy Research, vol. 7(1), p. 48-53, 2007.*
Kopta, "Psychometric evaluation of the behavioral health questionnaire-20: a brief instrument for assessing global mental health and the three phases of psychotherapy outcome," Psychotherapy Research, vol. 12(4), p. 413-426, 2002.*

* cited by examiner

*Primary Examiner* — G. Steven Vanni
(74) *Attorney, Agent, or Firm* — Gary K. Price

(57) ABSTRACT

Disclosed is a method of efficiently assessing the effectiveness of psychiatric medications as administered by physicians and more specifically to a methodology that compares the effectiveness of different medications across groups of patients based on changes in mental health scores using electronic systems. Additionally, the invention delineates when changes in medications are made during the course of medical visits for a single patient.

10 Claims, 8 Drawing Sheets

Please answer these questions as they relate to the past two weeks.
1. How distressed have you been with your life?

|  |  |
|---|---|
| Extremely distressed | (0) |
| Very distressed | (1) |
| Moderately distressed | (2) |
| A little bit distressed | (3) |
| Not at all distressed | (4) |

2. How satisfied have you been with your life?

|  |  |
|---|---|
| Not satisfied at all | (0) |
| Mildly satisfied | (1) |
| Somewhat satisfied | (2) |
| Satisfied | (3) |
| Very satisfied | (4) |

3. How energetic and motivated have you been feeling?

|  |  |
|---|---|
| Not at all energetic and motivated | (0) |
| A little bit energetic and motivated | (1) |
| Somewhat energetic and motivated | (2) |
| Energetic and motivated | (3) |
| Very energetic and motivated | (4) |

Please use the following rating scale:
- 0 Almost Always
- 1 Often
- 2 Sometimes
- 3 A Little Bit
- 4 Never In the past two weeks how much have you been distressed by:

|  |  |
|---|---|
| 4. Feeling fearful, scared. | (0) (1) (2) (3) (4) |
| 5. Alcohol/drug use interfering with your performance at school or work. | (0) (1) (2) (3) (4) |
| 6. Wanting to harm someone. | (0) (1) (2) (3) (4) |
| 7. Not liking yourself. | (0) (1) (2) (3) (4) |
| 8. Difficulty concentrating. | (0) (1) (2) (3) (4) |
| 9. Eating problem interfering with your relationships with your family or friends. | (0) (1) (2) (3) (4) |
| 10. Thoughts of ending your life. | (0) (1) (2) (3) (4) |
| 11. Feeling sad most of the time. | (0) (1) (2) (3) (4) |
| 12. Feeling hopeless about the future. | (0) (1) (2) (3) (4) |
| 13. Powerful, intense mood swings (highs and lows). | (0) (1) (2) (3) (4) |
| 14. Alcohol/drug use interfering with your relationships with family and/or friends. | (0) (1) (2) (3) (4) |
| 15. Feeling nervous. | (0) (1) (2) (3) (4) |
| 16. Heart pounding or racing. | (0) (1) (2) (3) (4) |

Please use the following rating scale:
- 0 Terrible
- 1 Poorly
- 2 Fair
- 3 Well
- 4 Very well How have you been getting along in the following areas of your life over the past two weeks? *Leave blank if the item does not apply.*

|  |  |
|---|---|
| 17. Nonfamily Social Relationships/Friends (for example, communication, closeness, level of activity). | (0) (1) (2) (3) (4) |
| 18. Life Enjoyment (for example recreation, life appreciation, leisure activities). | (0) (1) (2) (3) (4) |
| 19. Work/School (for example, performance, attendance). | (0) (1) (2) (3) (4) |
| 20. Intimate Relationships (for example support, communication, closeness). | (0) (1) (2) (3) (4) |

21. If you answered 0-3 on #10 above, please check below to indicate your overall risk of suicide.

|  |  |
|---|---|
| Extremely high risk | ___ (0) |
| High risk | ___ (1) |
| Moderate risk | ___ (2) |
| Low risk | ___ (3) |
| No risk | ___ (4) |

Fig. 1

(Prior Art)

ized clinical trial (RCT). The
ASSESSING THE EFFECTIVENESS OF PSYCHIATRIC MEDICATION IN PHYSICIANS' PRACTICES

CROSS REFERENCES TO RELATED APPLICATIONS

U.S. Provisional Application for Patent No. 61/338,290, filed Feb. 17, 2010, with title "Assessing the Effectiveness of Psychiatric Medication in Physicians' Practices" which is hereby incorporated by reference. Applicant claim priority pursuant to 35 U.S.C. Par. 119(e)(i).

BACKGROUND OF THE INVENTION

Field of Invention

This invention relates to a method of efficiently assessing the effectiveness of psychiatric medications as administered by physicians and more specifically to a methodology that compares the effectiveness of different medications across groups of patients based on changes in mental health scores using electronic systems. Additionally, the invention delineates when changes in medications are made during the course of medical visits for a single patient.

Description of Related Art

Regarding evaluating medication effectiveness for an individual patient, there are paper (e.g., Kopta, S. M., & Lowry, J. L., "Psychometric Evaluation of the Behavioral Health Questionnaire-20: A Brief Instrument for Assessing Global Mental Health and the Three Phases of Psychotherapy Outcome", Psychotherapy Research, 12, 413-426, 2002) and electronic questionnaires (e.g., "Behavioral Health Measure-20 within the CelestHealth System-MH; within the OQ Analyst") that assess mental health. Unfortunately, their use with medication treatments requires significant time and effort to associate questionnaire scores across medical visits with medication administration and changes in medication. For example, first, the patient is administered the paper-and-pencil questionnaire or an electronic questionnaire via computer. Second, the physician or staff must manually or electronically record the mental health score in the clinical notes or on a spread sheet and then record the type of medication administered. To detect changes in mental health over time, the notes must be reviewed date by date or the spread sheet visually scanned for changes in mental health scores. These changes would then have to be associated with the medication being administered at the time. This medication would also have to be entered into the notes or on the spreadsheet for the date of each visit.

There is no method available to systematically compare the effects of different medications across all patients in the physician's practice.

For years, pharmaceutical companies and universities have been comparing medication effectiveness using the research method of the randomized clinical trial (RCT). The typical RCT involves several steps (a) administering a psychiatric drug, a psychotherapy, or placebo pill to research subjects who are randomly assigned to two or more treatment conditions; (b) assessing the subjects' mental health at each medical visit using a questionnaire administered by paper or an electronic process (e.g., computer); (c) statistically analyzing the subjects' scores on the questionnaire; (d) based on these analyses, displaying the percent of subjects improved (i.e., percent of patients free of recurrence) across weeks for the medications being assessed in the RCT. This type of research provides information on medication effectiveness.

Software products are available that monitor across weeks the mental health of Individual subjects who are on a medication as prescribed in RCTs. These systems can also calculate the effectiveness of a single medication for groups of subjects. For example, Medical Outcome Systems, Inc. supports research studies and clinical trials by, among other things, providing graphs that display a mean mental health score on the ordinate with week number on the abscissa for a single subject and for all subjects participating in the RCT.

To understand the effectiveness of the medications that they administer, physicians rely on academic journals that publish the results of these RCTs. However, the RCT approach to evaluating medication effectiveness has been criticized along several lines. First, most RCTs are conducted by the pharmaceutical companies who sell the medications which are tested. These companies are not required to publish findings that are unfavorable to their product; therefore, there are concerns about the validity of the effectiveness claims made in many medication studies. Second, since most RCT subjects suffer from only one syndrome such as anxiety or depression, they do not represent the typical patient population seen by physicians in the real world. In contrast, the typical patient seen at the physician's office suffers from a combination of syndromes such as depression with panic attacks or depression with an eating disorder. These patients usually require a combination of drugs rather than just one medication. Additionally, practicing physicians do not have the time, staff, or statistical resources to assess in RCT fashion the effectiveness of medications that they actually prescribe to their patients.

SUMMARY OF THE INVENTION

In one aspect, the invention relates to a method of efficiently assessing the effectiveness of psychiatric medications as administered by physicians and more specifically to a methodology that compares the effectiveness of different medications across groups of patients based on changes in mental health scores. Additionally, the invention delineates when changes in medications are made during the course of medical visits for a single patient.

The present invention and its advantages over the prior art will become apparent upon reading the following detailed description and the appended claims with reference to the accompanying drawings.

BRIEF DESCRIPTION OF THE DRAWINGS

The above mentioned and other features of this invention will become more apparent and the invention itself will be better understood by reference to the following description of embodiments of the invention taken in conjunction with the accompanying drawings, wherein:

FIG. 1 shows a prior art Behavioral Health Measure.

DETAILED DESCRIPTION OF EXEMPLARY EMBODIMENTS

The invention will now be described in the following detailed description with reference to the drawings, wherein preferred embodiments are described in detail to enable practice of the invention. Although the invention is described with reference to these specific preferred embodiments, it will be understood that the invention is not limited to these preferred embodiments. But to the contrary, the invention includes numerous alternatives, modifications and equivalents as will become apparent from consideration of the following detailed description.

The present system, CelestHealth System-MD (CHS-MD) is a software product that electronically monitors, across visits, the effectiveness of psychiatric medications for an individual patient and also compares, across weeks, the effectiveness of different medications for all patients in the physician's practice. Using the Behavioral Health Measure-20 (BHM-20; see FIG. 1), the CHS-MD evaluates complete mental health in less than 2 minutes.

Medication Outcome Graph: Monitoring Medication Effectiveness for the Individual Patient At each medical visit, the patient electronically completes the Behavioral Health Measure-20 (BHM-20; see FIG. 1) that is appropriate for the patient's Dependent Variable, as will be discussed, on a computer through the CHS-MD website. The questionnaire is electronically scored using a standardized weighted scoring method known in the industry, generating a score between 0-4.

Figure 2:
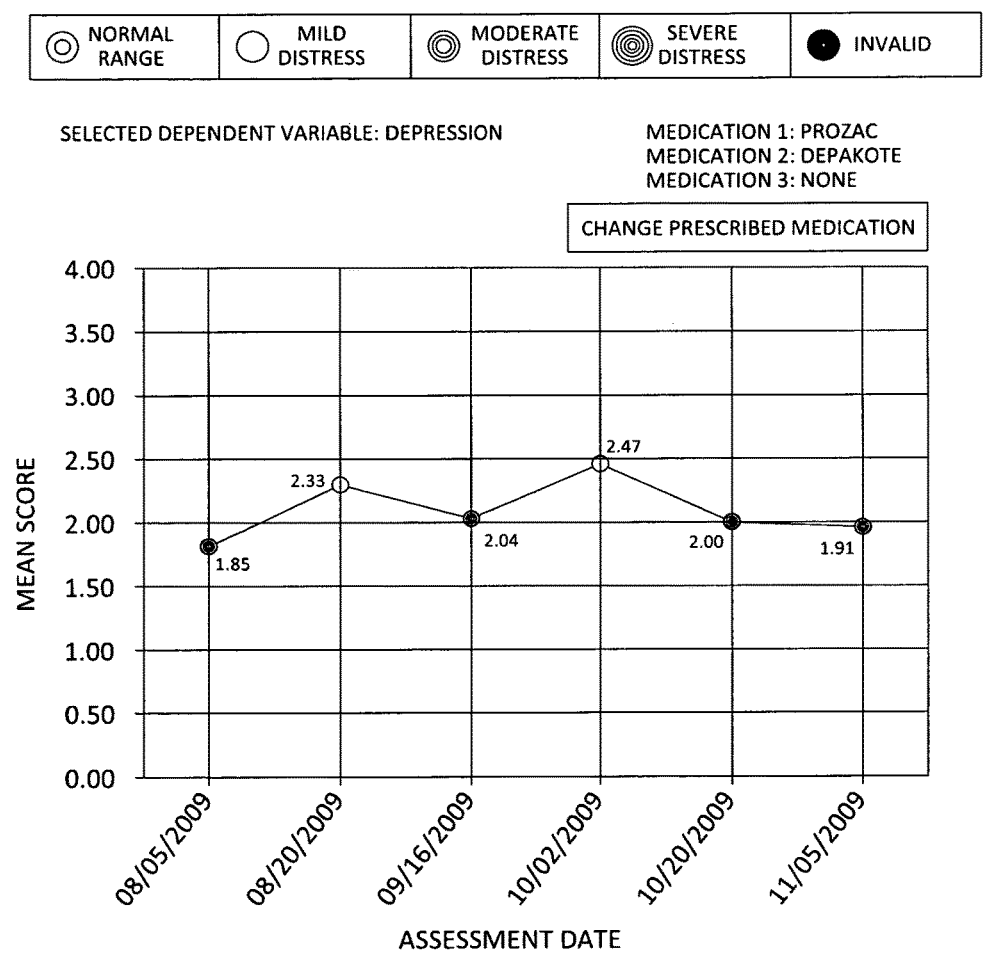
FIGS. 2-8 illustrate a method that compares the effectiveness of different medications across groups of patients based on changes in mental health scores and delineates when changes in medications are made during the course of medical visits for a single patient according to an embodiment of the invention. In the preferred embodiment, data and information for individuals is collected and stored an electronic system such as a computer database. The data is appropriately combined to create measures to efficiently assess the effectiveness of psychiatric medications.

As will be described, after the patient completes the questionnaire, the physician immediately receives electronic output pages that indicate the patient's current mental health status (based upon the patent's generated score) and the medication that s/he is currently taking. FIG. 2 shows the Medication Outcome Graph page (MOG) which depicts the BHM-20 mental health score (on the ordinate) across visits (on the abscissa). This information is available for at least 12 psychiatric variables that can be chosen from the Dependent Variable options which include:

| | |
|---|---|
| Global Mental Health | Depression |
| Well-Being | Eating Disorder |
| Symptoms | Panic Disorder |
| Life Functioning | Suicidality |
| Alcohol Drug Abuse | Violence Towards Others |
| Anxiety | Bipolar Disorder |

This page also provides a list of medications prescribed by the physician; they are labeled Medication 1, Medication 2, and Medication 3. Although three (3) medications are shown for example, additional medications and treatments could be tracked as well.

Figure 3:
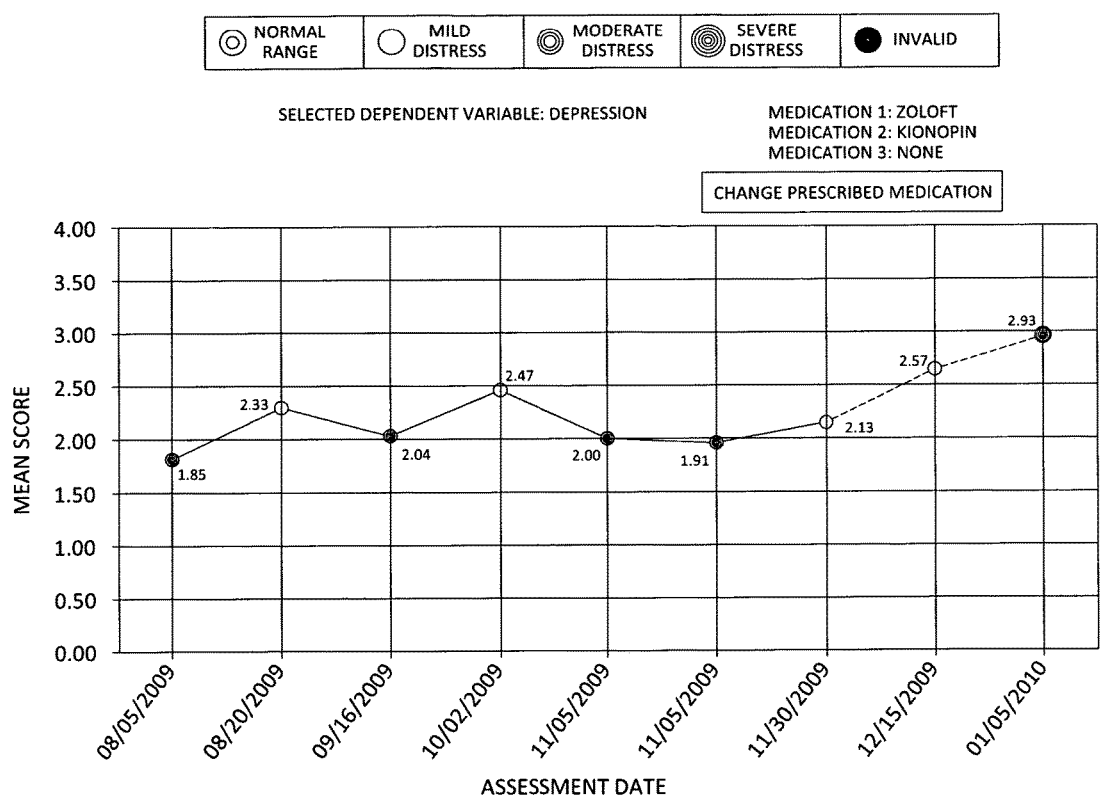

For example, FIG. 2 shows a patient with Dependent Variable option listed as "Depression", and generated score for each of the first six treatment visits during which the patient was taking Medication 1: Prozac, and Medication 2: Depakote. When a medication is changed at a specific visit, the physician selects the "Change Prescribed Medication" and selects charged medication from a list of medications stored that are used to treat the selected Dependant Variable, for example, Buspar for anxiety, Zoloft for depression, and Lamictal for bipolar disorder. As such, the system allows the physician to monitor the effects of particular medications and make changes to one to three medications or more at a time. Referring to FIG. 3, it is illustrated where at the seventh visit, the physician has changed the medication from Prozac and Depakote to Zoloft and Klonipin. At the same time, the trend line changes from a first color, blue at visits 1-6 to a second color, yellow at visits 7-9.

In addition to color changes other indicia could be used to note a change such as dashed, dotted or lettered lines for example. The result is a visual que on the graph that makes changes over time easy to see. A patient could possibly be seeing more than one doctor; for example, the patient on FIG. 3 might be seeing a general practitioner, a neurologist and a psychiatrist, and each might be independently changing some medications. The graph tracking method makes communication of changes easier to track between medical practitioners in the same system or across systems. It would not be unusual for a mental health patient with other health issues to be taking 6-10 medications that might have various interactions.

The colored data points on the trend line correspond to the statistically determined four levels of mental health Severe Distress (red), Moderate Distress (orange), Mild Distress (yellow), and Normal Range (green). The number at the data point is the patient's specific score for that treatment visit (see FIG. 2). And, touching a data point with the mouse pointer on the output device shows the medication being taken at that visit (see FIG. 3).

Using the MOG, the physician and patient receive immediate effectiveness feedback by viewing the BHM-20 scores for the prescribed medications across visits. Thus, the present system determines the effectiveness of the medications administered to the patient across a plurality of visits. The method also immediately notes any change in medication at the treatment visit in which it occurs.

Medication Effect Graph: Comparing the Effectiveness of Different Medications for all Patients As noted above, through the present system, the patient completes the BHM-20, the responses are electronically scored, and then the MOG is created for viewing by the physician and patient. The MOG shows the patient's course of improvement across visits based on the medications s/he is taking and any changes made in these medications.

Figure 4:
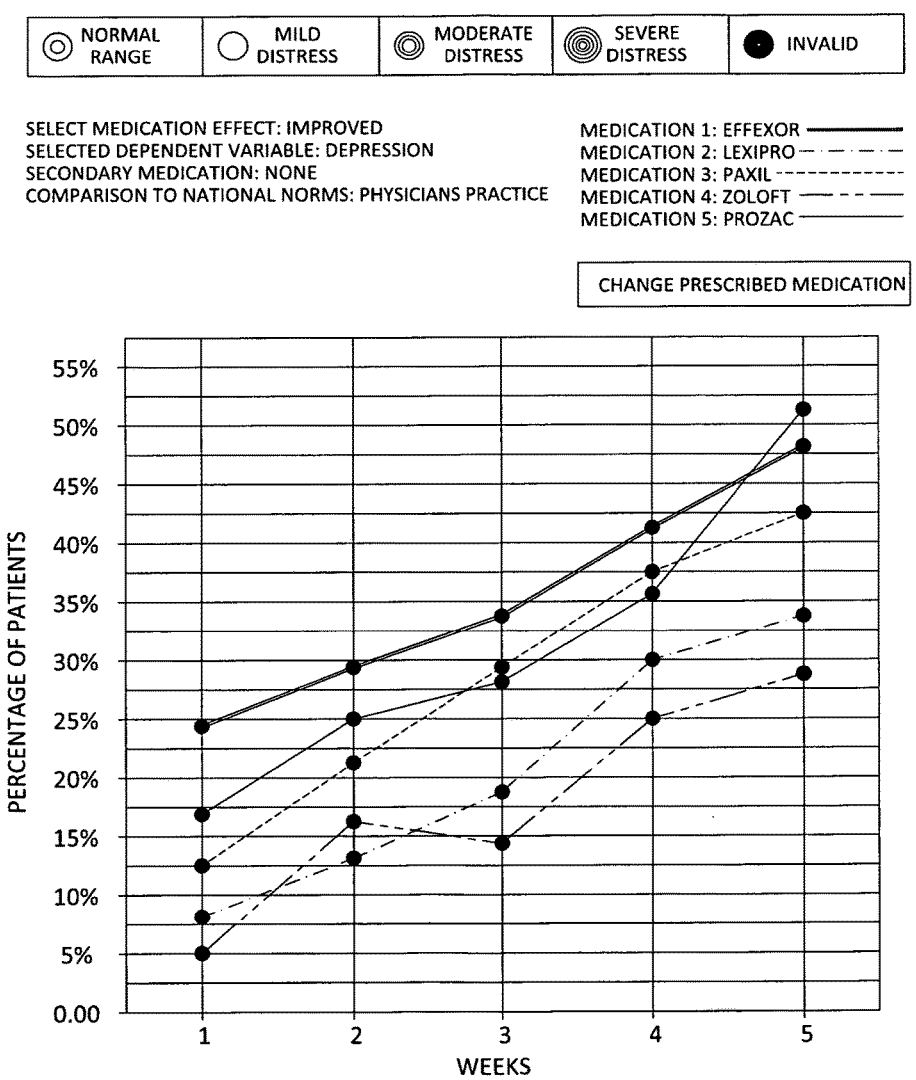

This patient outcome information is then statistically analyzed and combined with the same information from other patients in accordance with algorithms to create the Medication Effect Graph page (MEG; see FIG. 4). Such algorithms will generally include combining the total number of patients that (1) meet the selected criteria i.e., not in normal range at intake, selected medications, and dependent variable and (2) exhibit the requested medication effect, i.e., improved, recovered; divided by the total number of patients that meet the selected criteria. The MEG displays the effectiveness of the selected medications across weeks for all patients in the medical practice.

By electronic means, each patient's score on each of the at least 12 psychiatric variables is compared to statistically determined cut-off criteria with the patient classified as improved (I), recovered (R) or unimproved (U).

For each of the physician's patients, the week number (e.g., week #1, week #2, etc.) of treatment is calculated. Next, the number of patients who improve or recover at each specific treatment week number is divided by the total number of patients treated at that specific treatment week number; the resulting value is a percentage of patients improved or recovered for each treatment week number.

The MEG displays this information with percent of patients improved or recovered shown on the ordinate and week number on the abscissa.

As shown in FIG. 4, with input options for the physician including (a) Dependent Variable; (b) Medication Effect Improved or Recovered; (c) Medication 1; (d) Medication 2; (e) Medication 3; (f) Medication 4; (g) Medication 5; (h) Secondary Medication; and (i) Comparison to National Norms, and means for operating on the input responses, the physician can select up to five medications to compare for one graph. For example, in FIG. 4 the anti-depressant drug medications listed are: (a) Effexor, (b) Lexipro, (c) Paxil, (d) Zoloft, and (e) Prozac. For the dependent variable of Depression, there is shown five MEG lines in FIG. 4. Each line has a different color a first color, red; a second color, orange; a third color, yellow; a fourth color, green; and a fifth color, tan. These line colors correspond to the same colored frame around each of the five medications displayed. The data points are one color black. When the mouse pointer touches the data point on the output device, the system will display the number of patients assessed at that data point and the specific percentage of patients improved or recovered is shown (see FIG. 4).

Figure 5:
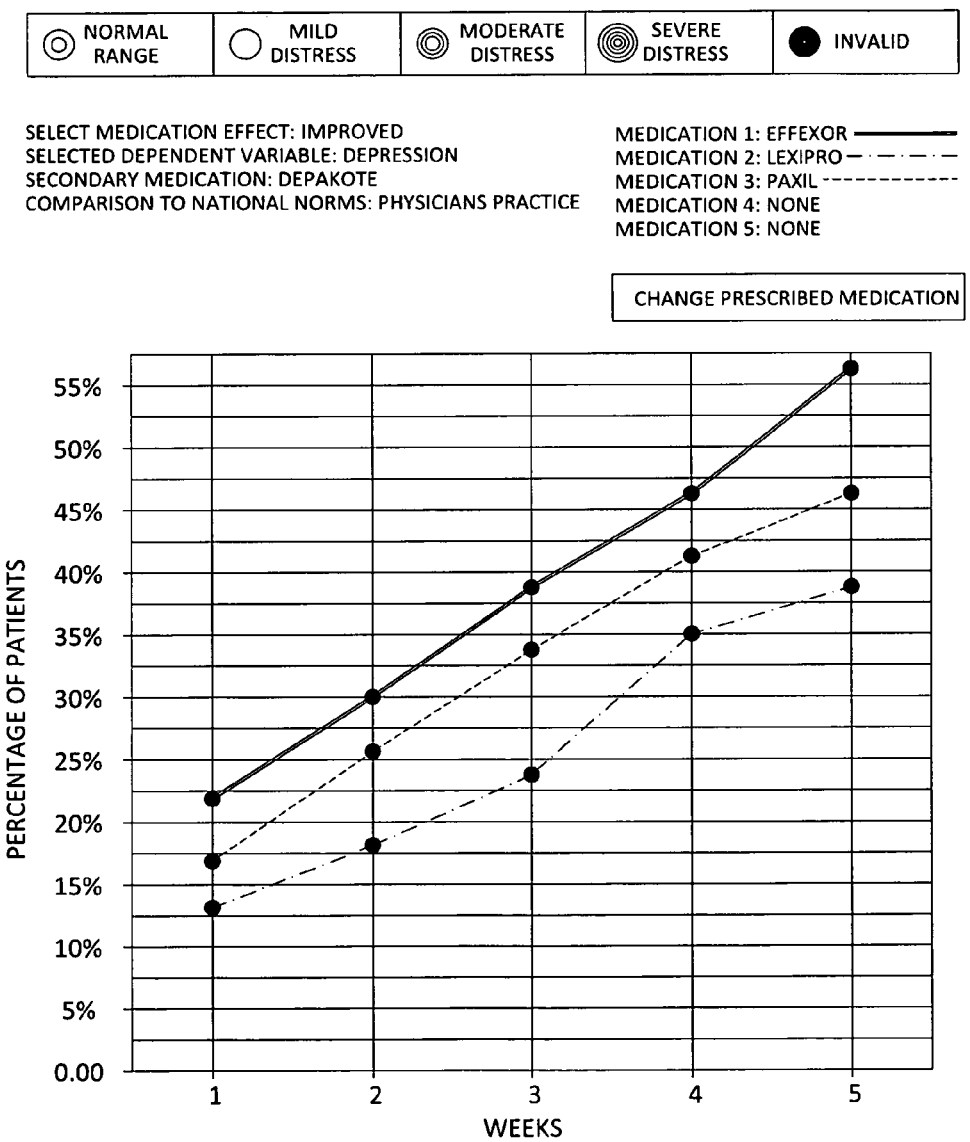

Additionally, a combination of two medications can be assessed for effectiveness. As shown in FIG. 5, three anti-depressant drugs (a) Effexor, (b) Lexipro, (c) Paxil are each combined with the mood stabilizer Depakote in the MEG. The Dependent Variable is again Depression. That is, for these patients, their physicians used one of the three anti-depressants with Depakote, as a secondary medication.

The system will also generate results based upon a selected physician's practice or based upon the results of all physicians entered "All practices." As such, if Physician's Practice is selected, the MEG information is based on patients in the specific physician's practice or specific group practice. If All Practices are selected, then the MEG information is processed using all medical practices in the present system.

The MEG information is updated in the system according to a specific time period, for example, every 24 hours. Thus, the MEG provides medical effectiveness information in the form of a living, dynamic process.

Figure 6:
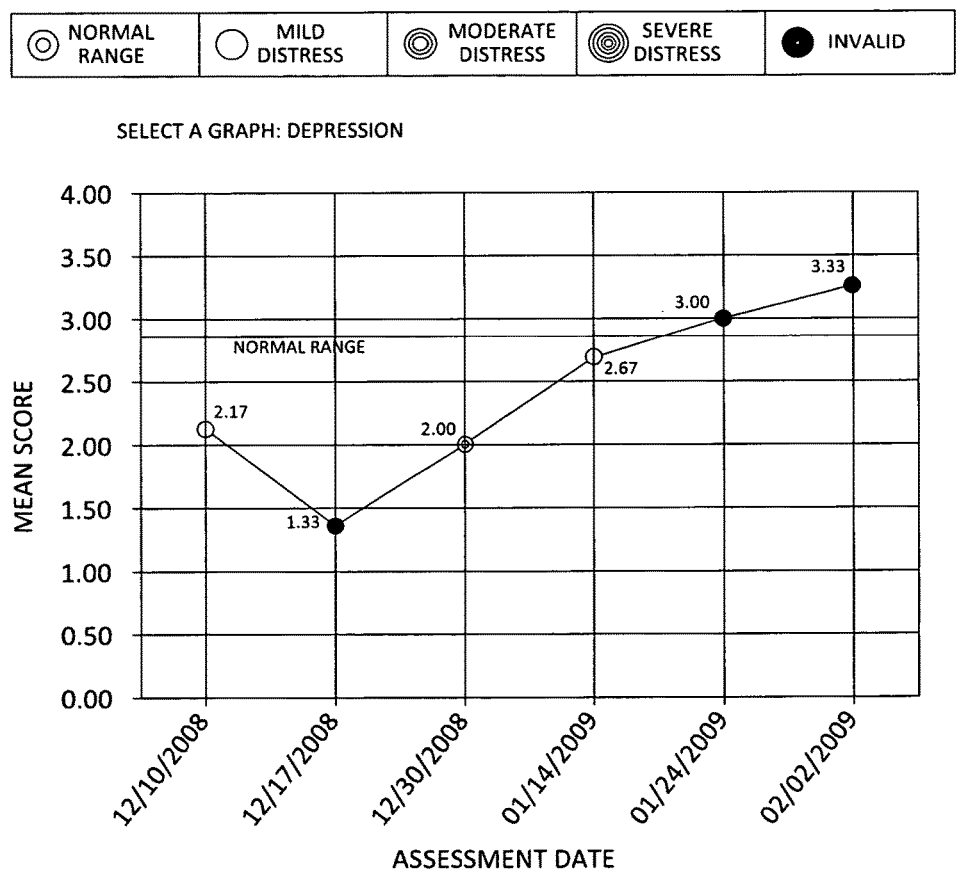
Figure 7:
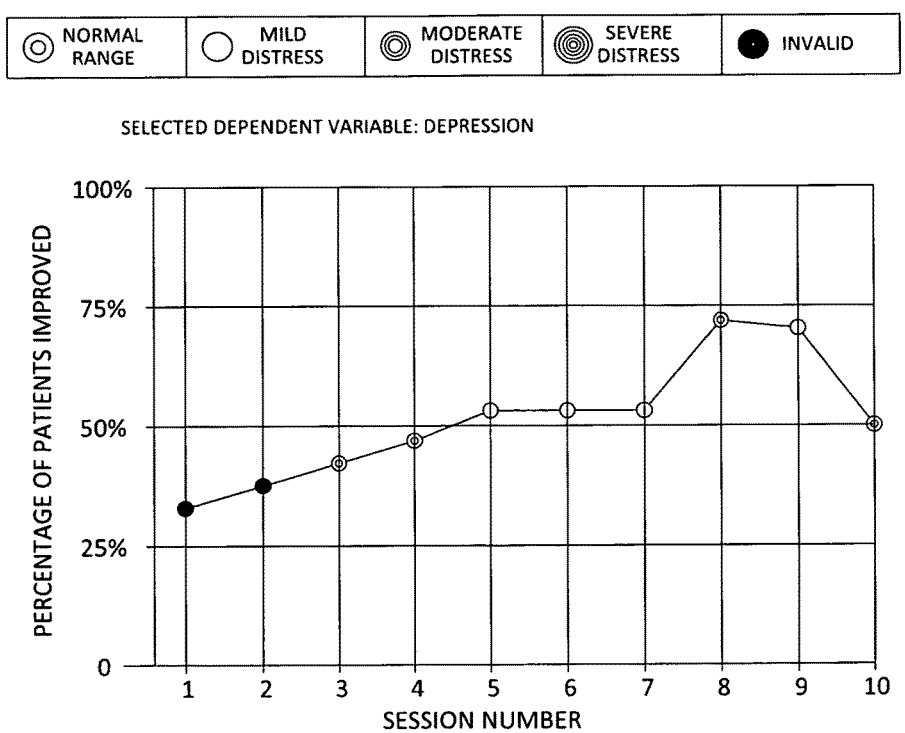

Software systems that electronically assess the mental health of an individual patient are already available as commercial products. Regarding an individual patient, the CelestHealth System-MH assesses the effectiveness of psychotherapy as a singular, generic treatment process across sessions and allows selecting the relevant Dependent Variable. It provides a psychotherapy outcome graph with date on the abscissa and mental health score on the ordinate (see FIG. 6). Additionally, regarding a group of patients, the system shows psychotherapeutic effectiveness across sessions for all patients in a private psychotherapy practice. It provides a psychotherapy effect graph with session number on the abscissa and percentage of patients improved or recovered on the ordinate (see FIG. 7).

The present system is different from the prior art because in addition to monitoring mental health across visits, it monitors mental health across visits for combinations of medications as well as changes in medication for the individual patient which are immediately displayed on the electronic MOG page. Whereas prior art systems may have the capability to monitor the effectiveness of combinations of mental health treatments for an individual patient across visits, they do not delineate changes in these treatments during the treatment process. Uniquely, the present system's monitoring method allows the physician to input medication options that immediately delineate which medications are being prescribed for the patient and any changes in these medications as they occur during treatment visits. This information is displayed in the MOG (see FIGS. 2 and 3).

The present system has the capability to immediately collect medication effect data from many physicians' practices and for a specific time period (e.g., every 24 hours) automatically create MEG's based on the national, normative data base that is characterized by large numbers of patients treated in all practices using the system. These graphs can be automatically updated according to the time period as data from the many practices continue to be input into the system. This process provides a living, dynamic display of medication effectiveness findings. There are no medication or psychotherapy evaluation systems that collect and analyze data in this fashion. The OQ Analyst does offer a graph showing national norms from different settings such as inpatient mental health, outpatient mental health, and employee assistance; however, the data is collected only once at a specific point in time and remains static in value. The data for these norms are not changing due to the repeated input of data as is capable with the present system. An example of the benefits of this kind of system not currently possible would include detection of counterfeit drugs. On rare occasions drugs have been counterfeited and these instances can go undetected for years. With the present system, if counterfeit Depakote for example, were introduced in a community, all patients taking the drug would likely suddenly experience negative effects. With the current invention a graph of all patients in a practice would have a good chance of showing a counterfeit drug in just a few weeks. The system can be set to automatically detect positive or adverse changes of a certain percentage of a doctor's patients or a percentage change of a doctor's patients versus a larger group such as a national group.

The present system has at least two unique capabilities. First, it provides a monitoring system that allows the physician to immediately delineate on the MOG electronic page which medications are being prescribed for the patient and make any changes in these medications as they occur across treatment visits. These changes are displayed on the MOG. Second, medication effectiveness data from all physicians' practices using the system which create a national, normative data base are displayed on the MEG and function as a living, dynamic process. This information is automatically updated according to a specific time period for example, every 24 hours as new data is inputted into the system.

The CHS-MD's methodology has the capability to assess the effects of medications for other medical specialties. For example, in the area of pain management, instead of using a mental health questionnaire, a pain assessment questionnaire such as, the Dallas Pain Questionnaire (Lawlis, Cuencas, Selby, & McCoy, 1989) would be electronically administered to the patient at each visit. DPQ pain scores would be electronically calculated and presented in the MOG format that includes four color-coded levels of pain severe (red), moderate (orange), mild (yellow), and none (green). The medication drop down menus would list medications for controlling pain for example, Vicodin, Percocet, OxyContin rather than psychiatric medications. The dependent variable drop down menu would feature the scales of the DPQ as variables for example, Daily Activities, Work/Leisure, Anxiety/Depression, and Social Activities rather than psychiatric variables. The physician would monitor the patient's pain scores instead of mental health scores across visits. He would use the MOG to help in his decision to continue or change medications and would use the MEG to help in decisions about which medications are best for which types of pain.

Figure 8:
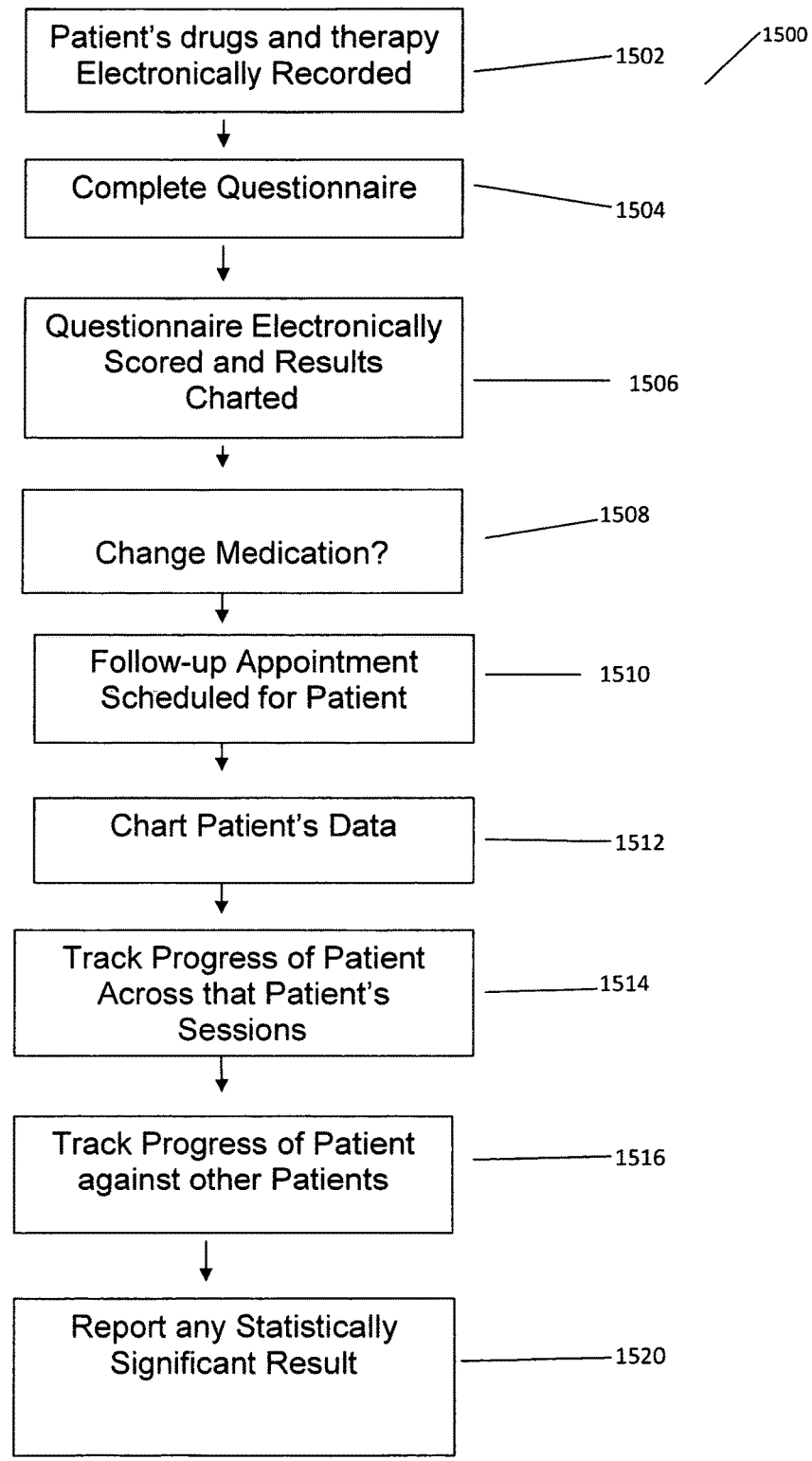

FIG. 8 shows the steps of the method 1500. The drugs and therapy a patient is currently on are electronically recorded 1502. The patient can then complete an electronic health survey questionnaire 1504. The questionnaire is scored electronically 1506 and the results are automatically and electronically charted. Based on the questionnaire examination and past data, the physician will make a decision to change medication 1508. A follow-up appointment will be scheduled 1510 and data will be charted for the patient 1512. An algorithm will be applied to track progress of patient across that patient's sessions 1514, against other patients on the same treatment and having the same doctor 1516, and results are compared against a population such as patients taking the drug nationally. If the system detects a statistically significant result 1520 such as one patient doing much worse than others in a population then that result will be automatically flagged for the doctor to provide further follow-up.

While this invention has been described in conjunction with the specific embodiments described above, it is evident that many alternatives, combinations, modifications and variations are apparent to those skilled in the art. Accordingly, the preferred embodiments of this invention, as set forth above are intended to be illustrative only, and not in a limiting sense. Various changes can be made without departing from the spirit and scope of this invention.

I claim:

1. A computer-assisted method of monitoring effective medication treatment including the steps of:
    a physician providing a patient at each of the patient's visits with a computer based mental health questionnaire;
    electronically storing the patients response to said questionnaire;
    generating a score based upon the patient's response, wherein said score indicates the patient's current mental health;
    electronically displaying a medication outcome graph that is configured to illustrate the patient's outcome information, wherein the patients outcome information includes the patients score and the patients prescribed medications from a set of medication choices used for treating the patient's current mental health, wherein said medication outcome graph is configured for the physician to monitor the patient's current mental health and prescribed medications during a selected time period during the patients visits and is configured to identify changes in the patient's outcome information during said selected time period;
    the physician tracking a treatment process for the patient by reviewing the medication outcome graph, wherein the computer-assisted method electronically enables the physician to modify the patient's prescribed medications from the set of medication choices;
    electronically assigning a patient classification based upon the patients score and a cut-off criteria;
    combining the patients outcome information with outcome information of other patients;
    electronically selecting those other patients having the patient's current mental health that have been taking a medication selected by the physician from the medication choices for the same period of time as the patient;
    electronically determining an outcome percentage for each week during the period of time by accumulating the total number of selected other patients that have a patient classification selected by the physician and dividing by the total number of selected other patients;
    electronically displaying a medication effect graph that is configured to illustrate how the selected other patients have responded for each week during the period of time to the selected medication; and,
    the physician monitoring the effectiveness of the patient's prescribed medications by visually reviewing the medication outcome graph illustrating the patient's current mental health for each week during the selected time period and the medication effect graph illustrating the outcome percentage of the selected other patients having the patient's current mental health and taking the selected medication.

2. The method as recited in claim 1, wherein said medication outcome graph shows a first trend line illustrating the patient's outcome information, said medication effect graph shows a second trend line illustrating said outcome percentage of the selected other patients, and including the step of electronically flagging the physician when said first trend line is different from said second trend line.

3. A computer-assisted method of monitoring effective medication treatment including the steps of:
    a physician providing a current patient with a computer based questionnaire at each of the patient's visits;
    electronically storing the current patient's response to said questionnaire;
    generating electronic output pages configured to indicate the current patient's mental health based upon the current patient's response to said questionnaire and the current patient's prescribed medications:
    accumulating a total number of weeks the patient has been taking each of the prescribed medications;
    electronically assigning a patient classification based upon the current patient's response to said questionnaire;
    electronically reviewing other patients medical records reported by physicians and selecting those other patients having the same current patient's mental health and taking a medication selected by the physician from a set of medication choices used for treating the current patient's mental health and taking the selected medication for a selected number of weeks, and wherein the selected number of weeks is greater than the total number of weeks;
    determining an outcome percentage for each week during the selected number of weeks by electronically accumulating the total number of selected other patients for each week that have a patient classification selected by the physician and dividing by the total number of selected other patients;
    electronically displaying a medication effect graph that is configured to illustrate how the selected other patients have responded to the selected medication each week during the selected number of weeks;
    the physician monitoring the effectiveness of the prescribed medications the current patient is taking by visually reviewing the current patient's electronic output pages illustrating a treatment process for the current patient with the current patient's prescribed medications and the medication effect graph illustrating a treatment process for each week during the selected number of weeks for the selected other patients taking the selected medication; and,
    the physician modifying on the electronic output pages said prescribed medications the current patient is taking in response to the monitoring the effectiveness step.

4. The method as recited in claim 3, wherein when said prescribed medications are modified, said electronic output pages are configured to include said modifying.

5. The method as recited in claim 4, wherein said electronic output pages include a first trend line that illustrates the current patient's treatment process during a selected number of current patient visits and said medication effect graph includes a second trend line that illustrates the selected other patients treatment process for each week during the selected number of weeks.

6. A computer-assisted method of monitoring effective medication treatment including the steps of:
- a physician providing a current patient at each of the patient's visits with a computer based questionnaire;
- accumulating a total number of patient's visits;
- electronically generating a data point based upon the current patient's response to said questionnaire and electronically saving said generated data points for each of the patient's visits;
- assigning a patient classification based upon said data point;
- electronically selecting from a group of other patients those other patients that have the same data point for a treatment period having at least the total number of patient's visits and taking a medication selected by the physician from a set of medication choices;
- electronically determining an outcome percentage for each week during the treatment period by accumulating the total number of selected other patients for each week that have a patient classification selected by the physician and dividing by the total number of selected other patients;
- electronically displaying a medication effect graph that is configured to illustrate how the selected other patients responded to the selected medication each week during the treatment period;
- the physician monitoring the effectiveness of the selected medication by visually reviewing the medication effect graph illustrating the percentage of selected other patients' progress taking the selected medication each week during the treatment period;
- modifying the same medication for the current patient in response to said monitoring the effectiveness step, wherein the computer-assisted method electronically enables the physician to modify the medication based upon the set of medication choices; and
- prescribing the modified medication for the current patient.

7. The method as recited in claim 6, wherein the step of electronically generating a data point includes electronically tracking said data point on a first trend line displayed on a medication outcome graph, said first trend line displaying each of the current patient's saved generated data points indicating how the current patient responded to the medication during the treatment period.

8. The method as recited in claim 7, wherein each of said saved generated data points on said first trend line is automatically assigned a color and each color corresponds to a level of health.

9. The method as recited in claim 8, wherein the step of electronically determining an outcome percentage includes electronically tracking said outcome percentage for each week during the treatment period on a second trend line displayed on said medication effect graph, wherein said second trend line is configured to illustrate how the selected other patients responded to the selected medication during each week of the treatment period.

10. The method as recited in claim 9, further including the step of electronically flagging the physician when said first trend line is different from said second trend line.

* * * * *